US008597307B2

(12) United States Patent
Miller

(10) Patent No.: US 8,597,307 B2
(45) Date of Patent: Dec. 3, 2013

(54) DISPOSABLE SUTURE CUTTER

(75) Inventor: Peter C. Miller, Largo, FL (US)

(73) Assignee: Linvatec Corporation, Largo, FL (US)

( * ) Notice: Subject to any disclaimer, the term of this patent is extended or adjusted under 35 U.S.C. 154(b) by 5 days.

(21) Appl. No.: 13/163,663

(22) Filed: Jun. 17, 2011

(65) Prior Publication Data

US 2011/0313430 A1 Dec. 22, 2011

Related U.S. Application Data

(60) Provisional application No. 61/356,270, filed on Jun. 18, 2010.

(51) Int. Cl.
*A61B 17/10* (2006.01)

(52) U.S. Cl.
USPC .......................................... 606/138; 606/167

(58) Field of Classification Search
USPC ........... 606/83, 138, 139, 144, 148, 159, 167, 606/170, 171, 172, 174, 175, 182; 30/286, 30/289, 294; 604/22
See application file for complete search history.

(56) References Cited

U.S. PATENT DOCUMENTS

| 3,802,074 A | * | 4/1974 | Hoppe ............................. 30/134 |
| 4,368,734 A | | 1/1983 | Banko |
| 5,176,691 A | * | 1/1993 | Pierce ........................... 606/148 |
| 6,254,620 B1 | | 7/2001 | Koh |
| 2006/0178682 A1 | | 8/2006 | Boehlke |
| 2006/0212045 A1 | | 9/2006 | Schilling |
| 2007/0106310 A1 | | 5/2007 | Golden |
| 2008/0195129 A1 | | 8/2008 | Weber |
| 2010/0069922 A1 | | 3/2010 | Kaufman |
| 2010/0087857 A1 | * | 4/2010 | Stone et al. .................... 606/232 |

FOREIGN PATENT DOCUMENTS

| EP | 0 569 256 A1 | 11/1993 |
| WO | 93/04635 A1 | 3/1993 |
| WO | 98/12970 A1 | 4/1998 |

* cited by examiner

*Primary Examiner* — Dianne Dornbusch
*Assistant Examiner* — Robert Lynch

(57) ABSTRACT

A suture cutting device is provided, the device suitable for cutting high strength suture materials used in arthroscopic surgeries. The device includes a distal blade portion movable within a distal suture guide, the distal suture guide including a lateral suture guide slot. The distal blade portion includes a dorsal recess that, in combination with an upper wall of an enclosed blade guide slot, controls an amount of dorsal movement of a cutting edge during a longitudinal movement of the cutting edge. The combined dorsal movement and longitudinal movement of the cutting edge creating a sliding/slicing movement of the cutting edge against a suture in the suture guide slot. At least a proximal blade portion and an extension blade portion are made of a single blade, those portions defining a spring, contacting a trigger, and effectuating a movement from a first position to a second position.

27 Claims, 4 Drawing Sheets

DISPOSABLE SUTURE CUTTER

TECHNICAL FIELD OF THE INVENTION

This invention relates to the design and use of a surgical instrument. The present invention relates particularly to a disposable surgical suture cutting device that is capable of cutting high strength sutures at a distance from a surgeon's hand and in confined spaces, such as during an arthroscopic surgery.

BACKGROUND OF THE INVENTION

Surgical sutures are used as part of nearly every surgical procedure. Even though the medical industry typically uses the generic term "suture" to describe a filament used in these surgical procedures, suture material varies greatly depending on the task to be accomplished.

Looking at sutures from a broad perspective, the strength of available suture materials varies greatly. For example, suture material used to dose and hold together tissue does not need to be much, if any, stronger than the surrounding tissue. Due at least in part to their relatively low material strength, these suture materials are often easy to manipulate and are easy to cut by the medical professional. On the opposite end of this strength continuum, high strength stainless steel wire may be used as suture material in locations where two bones are being held together and where the difficulty of manipulating and cutting such a high strength wire can be tolerated.

Due to advancements in plastics, there are now suture materials being used that rival stainless steel wire in terms of strength while retaining the flexibility of lower strength materials. For example, ultra high molecular weight polyethylene is now being used as a non-absorbable suture in locations, such as knee, shoulder, and other connective tissue repairs, where the surrounding tissue and/or suture anchors can support the additional loads made possible by such a high strength suture material.

As mentioned briefly above, suture materials typically become harder to cut as their strength increases. Obviously, most any high strength material can be cut easily and reliably using large hand tools. Unfortunately, medical professionals are not typically provided with the luxury of having such a large are required to use such large tools, especially during laparoscopic and arthroscopic procedures.

As described in the prior art, such as US 2006/0212045, US 2008/0195129, and US 2010/0069922 there are a variety of small reposable and disposable suture cutters that utilize a knife edge passing between two support surfaces or that utilize a knife edge passing alongside a single, often sharpened, support surface. The knife edge in each of these devices moves in a single path of motion such that the knife edge shears the suture. This function may work reasonably well if and/or when the knife edge is sharp. Because the sharpness of the knife edge reduces more quickly as the suture material strength increases, a particular suture cutter may become quickly unreliable when used to cut the highest strength suture materials. This fact requires the medical professional to use more than one disposable suture cutter or reposable suture cutter during each procedure, resulting in higher costs for everyone involved.

In light of the forgoing, a new suture cutter is required that can reliably cut high strength suture materials throughout a procedure.

SUMMARY OF THE INVENTION

A suture cutter made in accordance with one embodiment of the present invention includes features resulting in a robust device capable of cutting high strength suture materials close to tissue in an aurthoscopic surgical environment.

In accordance with one embodiment of the present invention, a suture cutter includes a hollow shaft extending along a longitudinal axis between a proximal handle and a distal suture guide. The distal suture guide comprises: (i) an enclosed blade guide slot being aligned with the longitudinal axis and being defined in part by a ventrally facing upper wall; (ii) an open lateral suture guide slot being positioned distal to the blade guide slot and being defined in part by a dorsally facing lower wall; and (iii) a relief slot being aligned with said longitudinal axis and being positioned distal said suture guide slot.

A blade is provided that comprises an extension blade portion extending along said longitudinal axis between a proximal blade portion and a distal blade portion. The distal blade portion comprising a sharpened inclined cutting edge being inclined to face away from said upper wall of said blade guide slot, to face away from a dorsal edge of said distal blade portion, and to face toward said lower wall of said suture guide slot. The blade is longitudinally movable in relation to the suture guide slot between a first position and a second position. The proximal blade portion comprises (i) an arcuate portion ventrally extending from the extension blade portion of said blade and (ii) a spring extension ventrally extending from said arcuate portion, said spring extension providing a biasing force to at least partially effectuate a proximal longitudinal movement of said distal blade portion from said second position to said first position, said arcuate portion of said blade being configured to contact a trigger.

The dorsal edge of the blade comprises (i) a distal tall portion near said cutting edge, (ii) a inclined portion proximally adjacent said tall portion, and (iii) a ventrally recessed short portion proximally adjacent said inclined portion. Dorsal movement of the distal blade portion is limited by an interaction between at least the inclined portion and of the upper wall of the blade guide slot during longitudinal movement of said distal blade portion between the first position and the second position.

Depressing the trigger longitudinally urges the cutting edge against a suture in the suture guide slot. The cutting edge is dorsally displaced by a force of the cutting edge against the suture. At least the inclined portion of the dorsal edge is urged against said upper wall of said blade guide slot. The cutting edge slides against the suture as a result of the longitudinal movement of the cutting edge in coordination with the dorsal movement of the cutting edge.

DETAILED DESCRIPTION

Figure 1:
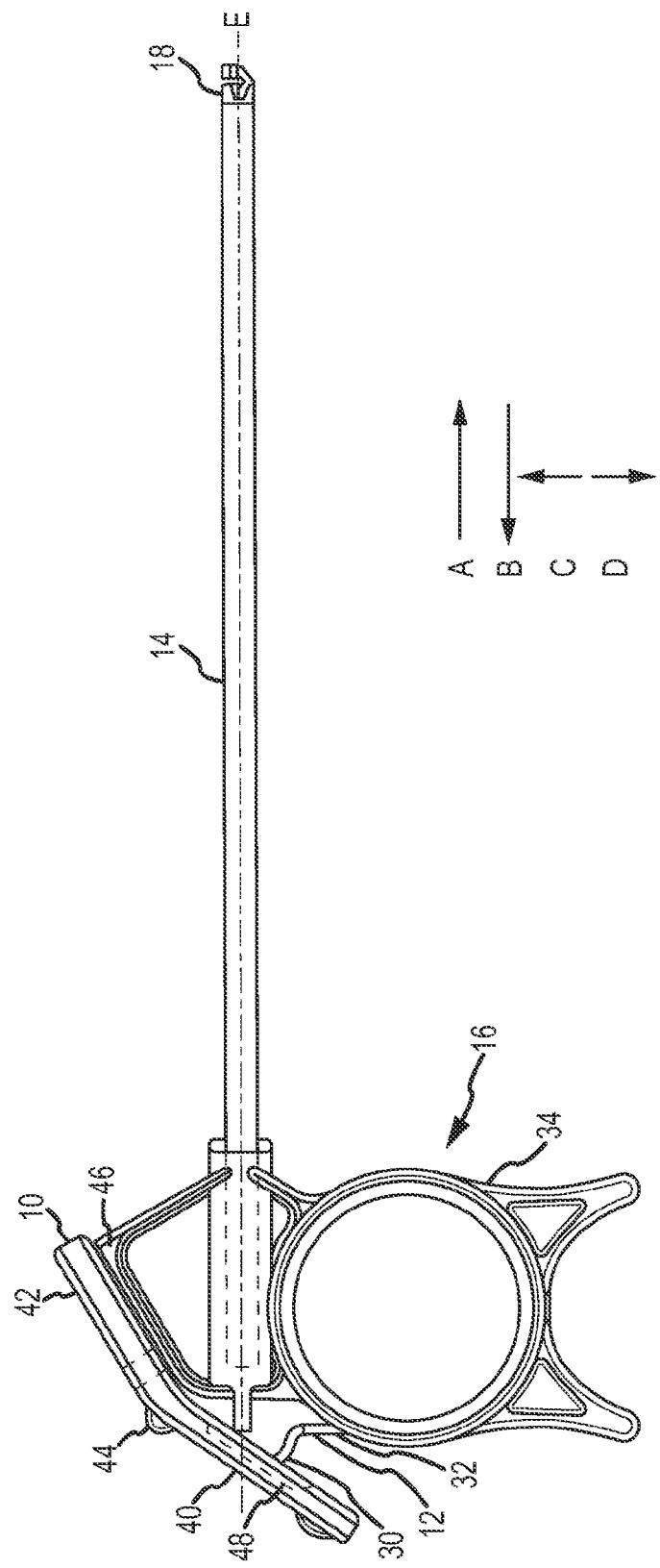
FIG. 1 is a side of one embodiment of the present invention.

A suture cutter device made in accordance with one embodiment of the present invention is represented in FIG. 1. For the purposes of the present description the relative directions "A", "B", "C", and "D" represented in FIG. 1 are defined as follows: the direction "A" will be referred to as "distal" or "distally"; the direction "B" will be referred to as "proximal" or "proximally"; the direction "C" will be referred to as "dorsal" or "dorsally"; and the direction "D" will be referred to as "ventral" or "ventrally". Further, the general longitudinal axis of the device is represented in FIG. 1 as axis "E".

Throughout the present description and figures, like reference numbers are used to identify similar features across all of the figures.

An embodiment of the present invention represented in FIG. 1 includes a hollow shaft 14 extending along longitudinal axis E. A handle 16 is positioned at a proximal end of the hollow shaft 14 and a suture guide 18 is positioned at a distal end on the hollow shaft 14. The handle 16 may be any of the well-known plastic materials which may be molded by injection molding or formed using any of the other well-known processes. One preferred example of such a material is ABS plastic.

The trigger 10, the function of which will be described further below, is attached to the handle 16 such that a fixed portion 42 of the trigger 10 is supported by the molded handle 16 and an extended, activation portion 40 of the trigger 10 is pivotable in relation to the fixed portion 42 generally about a pivot location 44. The fixed portion 42 of the trigger 10 rests against a fixed portion 46 of the molded handle 16 so that the suture cutter may be manipulated without activating the cutting mechanism (i.e., moving a one-piece blade 12 forward within the hollow tube 14). The fixed portion 42 may include an indentation to allow for a more positive contact with a surgeon's finger.

The handle 14 further includes finger grip features 34 opposite the trigger 10 to help stabilize and maneuver the suture cutter into a suitable location. To avoid an unintentional actuation of the device, it is envisaged that a surgeon will hold the device with a finger on the features 34 and a thumb on the fixed portion 42 of the trigger 10.

It is envisaged that the trigger 10 is of a material separate from the handle 16. It is envisaged that the trigger 10 could be formed of the same material (at the same time) as the handle 16, with the pivot location 44 being suitably thin to allow for the necessary pivot action without cracking or breaking the material at that location. The trigger 10 may be made of a material that provides for greater friction with a surgeon's thumb.

In the present embodiment, the shaft 14 is stainless steel tube, preferably 304 stainless steel. The primary purpose of the shaft 14 is to maintain a directional and rotational stability of the suture guide 18 and a blade 12 passing there through. While stainless steel performs the necessary function well and is a preferred material, the shaft 14 may be made of any of the other known structural metals, such as aluminum, carbon steels, etc. Further, the shaft 14 may be manufactured of an extruded structural plastic material, such as those impregnated with glass, carbon, and/or rigid plastic fibers.

The shaft 14 may be affixed to the handle 16 using any of the known techniques, as there will be relatively small axial separation forces and rotational forces transmitted from the handle 16 to the shaft 14. Accordingly, the handle 16 may be molded around the shaft 14 or the shaft 14 may be affixed later to the handle 16 through the use of an adhesive. It is envisaged that the shaft may be somewhat deformed or may be provided with a keying feature that provides additional resistance to axial and rotational forces at the joint between the shaft 14 and the handle 16. It is further envisaged that the shaft 14 may extend a significant distance within the handle 16 to provide additional strength to the joint and to provide additional stiffness to the handle 16.

The suture guide 18 in the present embodiment is preferably a separately molded, formed and/or machined piece that is affixed to the distal end of the shaft 14. It is envisaged that the suture guide will be an injection molded plastic, such as PEEK, with minimal subsequent machining to provide the preferred features described herein. Other forming techniques may also be used resulting in a similar outcome.

Figure 4:
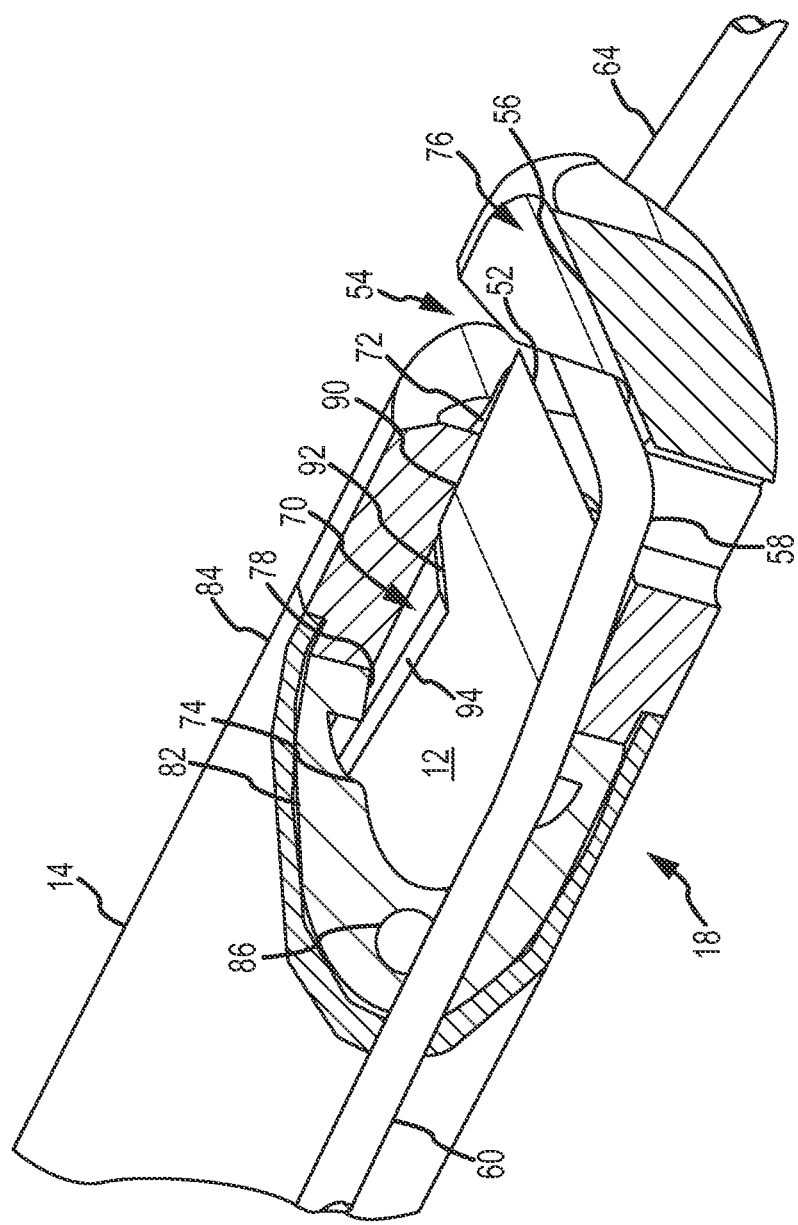
FIG. 4 is a partial section view of the suture guide and blade in FIG. 2.

As shown in FIG. 4, the suture guide 18 may include a proximal, reduced diameter portion 82 that passes into a distal end 84 of the shaft 14 to ensure a coaxial alignment of the suture guide 18 to the shaft 14. As discussed above in relation to the joint between the handle 16 and the shaft 14, relatively small axial and rotational forces will be passed from the shaft 14 to the suture guide 18. Accordingly, the suture guide 18 will likely need to be fixed, using an adhesive or mechanical crimp, to the distal end of the shaft 14. It is envisaged that a hole or depression 86 may be formed in the reduced diameter portion 82 of the suture guide 18 for the purpose of accepting a deformation, such as a crimp, (not shown) in the shaft 14 to retain the suture guide 18.

The blade 12 is slidably retained in the hollow shaft 14, with a distal blade portion extending into the suture guide 18 and a proximal blade portion extending through and along the handle 16. Note that the terms "distal blade portion" and "proximal blade portion" are being used throughout to represent the general end regions of the blade 12. These general terms are being used so as to not distract from the more specific features contained in those regions that will be discussed in greater detail below.

The proximal blade portion of the blade 12 is configured to cooperate with the trigger 10 and to provide a necessary biasing force. A recess 48 in the activation portion 40 of the trigger 10 partially traps a C-shaped arcuate portion 30 of the blade 12. An extension blade portion 32 of the one-piece blade 12 ventrally extends from the arcuate portion 30 and is attached to the handle 16 at a point sufficiently far from the arcuate portion 30 and the hollow tube 14 to allow the blade 12 to function as a spring.

A biasing force provided by the spring formed by the arcuate portion 30 and the extension blade portion 32 of the blade 12 maintains the blade 12 in a first position (i.e. the distal blade portion of the one piece blade 12 is fully retracted) and returns the blade 12 to the first position from a second position (i.e. position of the distal blade portion of the blade 12 after a cut is made but before the distal blade portion is retracted). As will be discussed in greater detail below, FIGS. 2 and 4 show the distal blade portion of the blade 12 in a position that is between the first position and the second position (i.e. a cut has been initiated but has not been completed).

It is envisaged that the one-piece blade 12 may be made a single, continuous strip of carbon or stainless steel. This is further envisaged that the single, continuous strip of carbon or stainless steel will include differing treatments along its length to instill different material properties. Further, it is envisaged that the blade 12 may be provided with a separable end cutting edge to allow for the use of a material that is best suited for maintaining a sharpened edge while the remaining portions of the blade are of a another continuous strip. The joint of such an arrangement may be located within the suture guide 18 such the suture guide 18 can help to maintain the joint, especially in an situation where a finger of one portion is interlocked within the other portion. Additionally, it is envisaged that a single treatment to the entire strip of blade material may be sufficient for the purposes and longevity of the present device.

In operation, the distal blade portion of the blade 12 may be actuated from the first position to the second position (discussed more fully below) by pushing distally on the activation portion 40 of the trigger 10 thereby distally pushing the arcuate portion 30, and therefore, distally pushing the remaining portions of the blade 12 (i.e. an extension blade portion within the hollow tube 14 and the distal blade portion) in relation to the hollow tube 14 and the suture guide 18. When the activation portion 40 of the trigger 10 is released, the radius portion 30 and the proximal extension blade portion 32 cause the blade 12 to retract in relation to the hollow tube 14 and the suture guide 18 and push the extended portion 40 of the trigger 10 back into a rest position. A stop device may be located at or near the pivot location 44 to prevent the activation portion 40 of the trigger 10 from proximally extending too far.

Figure 2:
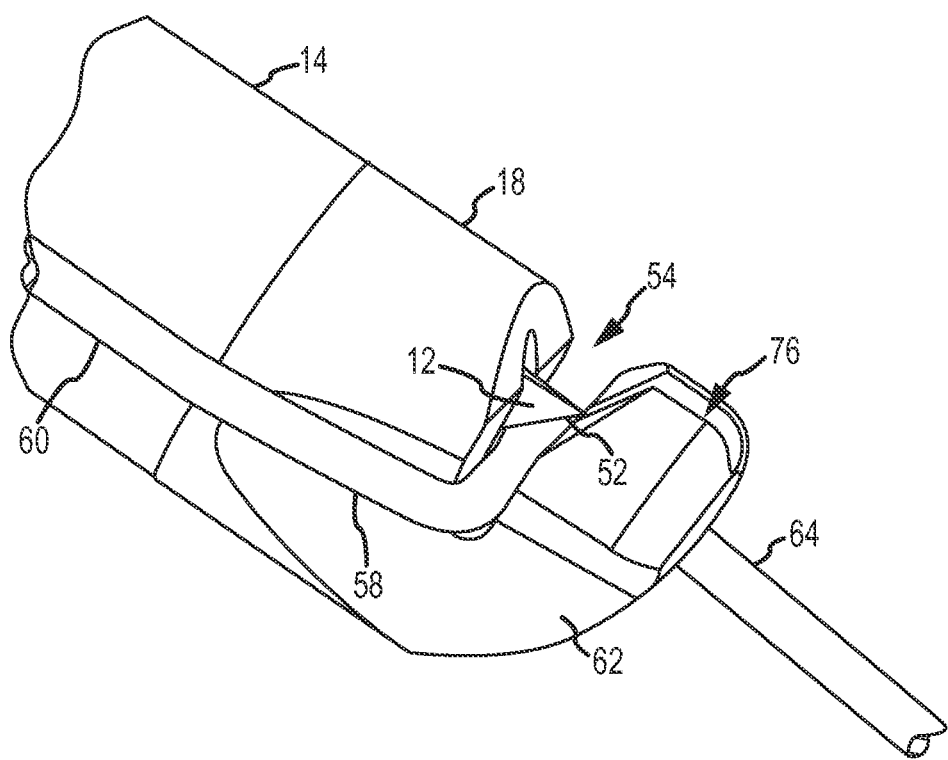
FIG. 2 is a dose perspective view of a suture guide and blade used in the embodiment in FIG. 1.

Referring now to FIGS. 2 and 4, a suture 58 may be positioned within an open lateral suture guide slot 54 of the suture guide 18. Note that the blade 12 is partially extended from an enclosed blade guide slot 74 such that the blade 12 is partially obstructing the suture's entry into the suture guide slot 54. The blade 12 would need to be retracted fully within to the first position such that the distal blade portion of the blade 12 does not extend from or does not extend far from the enclosed blade guide slot 18 to provide the necessary clearance allowing entry of the suture 58 into the suture guide slot 54.

Figure 3:
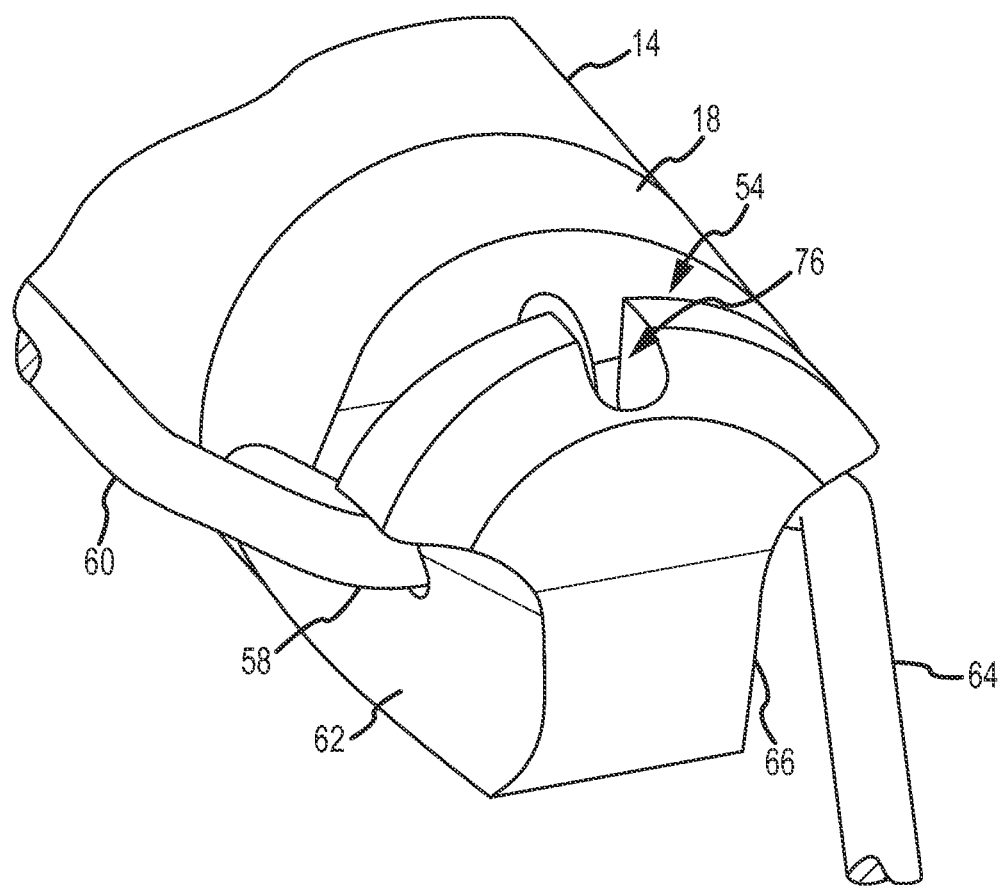
FIG. 3 is another dose perspective view of the suture guide and blade in FIG. 2.

The distal blade portion of the blade 12 includes a distal tip 50 having a sharpened inclined cutting edge 52. Once a suture 58 is placed in the suture guide slot 54, a proximally extending portion 60 of the suture 58 is received within a curved guide area 62, and a distally extending portion 64 of the suture 58 is received in another curved guide area 66 on an opposite side of the suture guide 18. Thus, as shown in FIGS. 2, 3 and 4, the suture 58 may take on a zigzag configuration. As is most easily seen in FIG. 3, each of the curved guide areas 62, 66 are deepest (i.e., greatest distance from a nominal outer diameter of the suture guide 18) at a distal extent of the suture guide 18. Each of the curved guide areas 62, 66 become shallower (i.e., a lesser distance from the nominal outer diameter of the suture guide 18) as the respective curved guide area 62, 66 extends proximally.

The curved guide areas 62, 66 may be provided on both sides of the suture guide 18 to allow cuts dose to an adjacent object. For example, during a surgery to repair meniscal tissue of a knee, sutures should be cut dose to the meniscal tissue such that little suture material extends beyond the tissue. Accordingly, if there is no need for cutting a suture dose to an object, the curved guide areas 62, 66 may not be necessary.

Once the suture 58 is in location within the suture guide slot 54, the distal blade portion of the blade 12 may be pushed distally using the trigger 10 such that the cutting edge 52 engages the suture 58. More specifically, the trigger 10 described in relation to FIG. 1 pushes the against the arcuate portion 30 of the blade 12 to move the cutting edge 52 with respect to the suture guide slot 54. As can be best observed in FIG. 4, continued advancement of cutting blade 12 cause the cutting edge 52 to push against the suture, but the inventors have discovered that pushing the cutting edge 52 directly only axially against the suture 58 may not effectuate a reliable cut, at least in part because the suture 58 may be made of an ultra-high molecular weight polyethylene and/or the cutting edge 52 may be dulled from previous cuts.

As best shown in FIG. 4, a clearance recess 70 has been provided in the present embodiment to augment the distal, axial force with dorsal movement of the distal blade portion of the blade 12. The dorsal movement of the cutting edge 52, along with the distal movement of the cutting edge 52 creates a sliding, slicing action of the cutting edge 52 against along the suture 58. In other words, the blade of the present embodiment may be allowed in a controlled manner, by design, to move in a dorsal direction separate from the distal movement along the longitudinal axis E of the hollow tube 14 in order to create a sliding, slicing action between the cutting edge 52 and the suture 58. To accomplish this controlled movement in the dorsal direction, the distal blade portion of the blade 12 is provided with the clearance recess 70 along a dorsal edge 72 of the blade 12 proximal to the cutting edge 52. The dorsal edge 72 of the blade 12 includes a tall portion 90 and a short portion 94 separated by an inclined portion 92, the short portion 94 and the inclined portion 92 making up the clearance recess 70 of the blade 12. In the first portion, the tall portion 90 of the blade 12 rest against or nearly against with the positioned adjacent the distal cutting edge lies against a ventrally facing upper wall 78 defining an upper extent of the blade guide slot 74 in which blade 12 resides. Once the blade 12 is distally pushed a sufficient distance toward the second position (i.e. where the suture 58 is severed), the tall portion 90 of the blade 12 will extend beyond the constraints of the guide slot 74 and the upper wall 78 such that the inclined portion 92 of the clearance recess 70 may contact the upper wall 78 of the blade guide slot 74. Accordingly, the interaction between the inclined portion 92 and possibly the short portion 94 of the dorsal edge 72 and the top wall of the guide slot allows the blade 12 to move dorsally away from a bottom wall of the blade guide slot 74 and in a direction incident to the longitudinal axis of the hollow tube 14 causing a slicing action as the cutting edge 52 is being pushed distally along the longitudinal axis. It is envisaged that the dorsal movement of the blade may occur at least in part by the force of the cutting edge 52 against the suture 58 in the suture guide slot. In other words, if a suture is not present in the suture guide slot, their my be little if any dorsal movement of the cutting edge 52 with the distal blade portion is moved from the firth position to the second position.

it is envisioned that the profile and depth of the clearance recess 70 may be optimized to effect and efficient cut on a particular suture. For example, at about the same time the inclined distal cutting edge 52 begins to press against the suture, the tall portion 90 passes the distal end of the upper wall 78 of the blade guide slot 74 allowing the cutting edge 52 of the blade 12 to begin its dorsal rise away from the bottom wall of the blade guide slot 74. Once the cutting edge 52 passes a point where the suture should be cut through, the short portion 94 (i.e., the deepest portion of the clearance recess 70) may be positioned to interact with the upper wall 78 of the blade guide slot 74. It should be understood that the clearance recess 70 may be deeper or shallower than described here, and further optimization may be required. It should also be understood that the clearance recess 70 may be the normal height of the blade 12 while the tall portion 90 may extend away from the normal height causing a similar result as creating a recess 70 shown. Similarly, it is envisaged that the upper wall 78 of the blade guide slot 74 may include some deviation in height further effectuating the described dorsal movement of the cutting edge 52.

An axially aligned relief slot 76 may be provided distal to the suture guide slot 54 in the suture guide 18 to help guide direct and protect the cutting edge 52 of the blade 12 during a distal displacement of the cutting edge 52. As shown in FIG. 4, a bottom wall 56 of the relief slot 76 may be inclined in some manner to help dorsally direct the cutting edge 52, if the suture 58 material or cutting edge 52 to not sufficiently defect the cutting edge 52 to create the sliding slicing action.

It will be understood by those skilled in the art that numerous improvements and modifications may be made to the preferred embodiment of the invention disclosed herein without departing from the spirit and scope thereof.

What is claimed is:

1. A surgical suture cutting device comprising:
   a hollow shaft extending along a longitudinal axis between a proximal handle and a distal suture guide, said suture guide comprising (i) an enclosed blade guide slot being aligned with said longitudinal axis and being defined in part by a ventrally facing upper wall, (ii) an open lateral suture guide slot being positioned distal to said blade guide slot and being defined in part by a dorsally facing lower wall, and (iii) a relief slot being aligned with said longitudinal axis and being positioned distal said lateral suture guide slot; and
   an blade comprising an extension blade portion extending along said longitudinal axis between a proximal blade portion and a distal blade portion, said distal blade portion comprising a sharpened inclined cutting edge being inclined to face away from said upper wall of said blade guide slot, to face away from a dorsal edge of said distal blade portion, and to face toward said lower wall of said suture guide slot, said distal blade portion being longitudinally movable in relation to said suture guide slot between a first position and a second position;
   wherein said dorsal edge of said distal blade portion comprises (i) a distal tall portion near said cutting edge, (ii) a inclined portion proximally adjacent said tall portion, and (iii) a recessed short portion proximally adjacent said inclined portion,
   wherein dorsal movement of said distal blade portion is limited by an interaction between at least said inclined portion and of said upper wall of said blade guide slot during longitudinal movement of said distal blade portion between said first position and said second position, and
   wherein said inclined portion of said dorsal edge is configured to be in contact with said upper wall of said blade guide slot for a predetermined longitudinal movement distance of said cutting edge such that dorsal movement of said cutting edge occurs simultaneously with said predetermined longitudinal movement distance.

2. A surgical suture cutting device according to claim 1 wherein said distal suture guide further comprises at least one curved guide area extending along a side surface of said distal suture guide, said curved guide area adjacent an end of said suture guide slot and extending distally and proximally from said suture guide slot along said distal suture guide.

3. A surgical suture cutting device according to claim 2 wherein a depth of said at least one curved guide area becomes more shallow extending proximally from a deepest portion at a distal extent of said distal suture guide.

4. A surgical suture cutting device according to claim 1 wherein said suture guide slot is defined in part by dorsal facing, distal and proximal chamfered surfaces arranged to ease an insertion of a suture into said suture guide slot.

5. A surgical suture cutting device according to claim 1 wherein said relief slot is defined in part by a lower wall being inclined to proximately and dorsally face toward said cutting edge, and wherein in said second position, said cutting edge is urged against said lower wall of said relief slot.

6. The surgical cutting device according to claim 1 wherein said predetermined longitudinal movement distance is at least an expected thickness of a suture to be cut such that said dorsal movement of said cutting edge occurs throughout a cutting said suture.

7. A surgical suture cutting device according to claim 1 wherein said proximal blade portion comprises an arcuate portion ventrally extending from said extension blade portion, said arcuate portion being configured to contact a trigger to effectuate a distal longitudinal movement of said distal blade portion from said first position to said second position.

8. A surgical suture cutting device according to claim 7 wherein said proximal blade portion further comprises a spring extension ventrally extending from said arcuate portion, said spring extension providing a biasing force to at least partially effectuate a proximal longitudinal movement of said distal blade portion from said second position to said first position.

9. A surgical suture cutting device according to claim 8 wherein said trigger is attached to said handle via a pivot which allows for a movement of the trigger to urge against said arcuate portion.

10. A surgical suture cutting device according to claim 8 wherein said proximal blade portion and said extension blade portion consist of a single length of blade material.

11. A surgical suture cutting device comprising:
    a hollow shaft extending along a longitudinal axis between a proximal handle and a distal suture guide; and
    a blade comprising an extension blade portion extending along said longitudinal axis between a proximal blade portion and a distal blade portion, said distal blade portion comprising a sharpened inclined cutting edge and being longitudinally movable between a first position and a second position, said proximal blade portion comprising (i) an arcuate portion ventrally extending from said extension blade portion and (ii) a spring extension ventrally extending from said arcuate portion, said spring extension providing a biasing force to at least partially effectuate a proximal longitudinal movement of said distal end portions of said blade from said second position to said first position, said arcuate portion of said blade configured to contact a trigger to effectuate a distal longitudinal movement of said distal blade portion from said first position to said second position,
    wherein said proximal blade portion and said extension blade portion consist of a single length of blade material.

12. A surgical suture cutting device according to claim 11 wherein said trigger is attached to said handle via a pivot which allows for a movement of the trigger to press against said arcuate portion.

13. A surgical suture cutting device according to claim 11 wherein said distal suture guide further comprises (i) an open lateral suture guide slot being defined in part by a distal lateral wall and a dorsally facing lower wall and (ii) at least one curved guide area extending along a side surface of said distal suture guide, said curved guide area adjacent an end of said suture guide slot and extending distally and proximally from said suture guide slot along said distal suture guide.

14. A surgical suture cutting device according to claim 13 wherein a depth of said at least one curved guide area becomes more shallow from a deepest portion at a distal extent of said distal suture guide.

15. A surgical suture cutting device comprising:
    a hollow shaft extending along a longitudinal axis between a proximal handle and a distal suture guide; and
    a blade comprising an extension blade portion extending along said longitudinal axis between a proximal blade portion and a distal blade portion, said distal blade portion comprising a sharpened inclined cutting edge and being longitudinally movable between a first position and a second position, said proximal blade portion comprising (i) an arcuate portion ventrally extending from said extension blade portion and (ii) a spring extension ventrally extending from said arcuate portion, said spring extension providing a biasing force to at least partially effectuate a proximal longitudinal movement of said distal end portions of said blade from said second position to said first position, said arcuate portion of said blade configured to contact a trigger to effectuate a distal longitudinal movement of said distal blade portion from said first position to said second position, wherein said distal suture guide comprises (i) an enclosed blade guide slot being aligned with said longitudinal axis and being defined in part by a ventrally facing upper wall, (ii) an open lateral suture guide slot being positioned distal to said blade guide slot and being defined in part by a dorsally facing lower wall, and (iii) a relief slot being aligned with said longitudinal axis and being positioned distal said suture guide slot, wherein the sharpened inclined cutting edge is inclined to face away from said upper wall of said blade guide slot, to face away from a dorsal edge of said distal blade portion, and to face toward said lower wall of said suture guide slot;

wherein said dorsal edge of said blade comprises a distal tall portion near said cutting edge, (ii) a inclined portion proximally adjacent said tall portion, and (iii) a ventrally recessed short portion proximally adjacent said inclined portion, and wherein dorsal movement of said distal blade portion is limited by an interaction between at least said inclined portion of said dorsal edge of said blade and of said upper wall of said blade guide slot during longitudinal movement of said blade between said first position and said second position, wherein said inclined portion of said dorsal edge is configured to be in contact with said upper wall of said blade guide slot for a predetermined longitudinal movement distance of said cutting edge such that dorsal movement of said cutting edge occurs simultaneously with said predetermined longitudinal movement distance.

16. The surgical cutting device according to claim 15 wherein predetermined longitudinal movement distance is at least an expected thickness of a suture to be cut such that said dorsal movement of said cutting edge occurs throughout a cutting said suture.

17. A surgical suture cutting device according to claim 15 wherein said proximal blade portion and said extension blade portion consist of a single length of blade material.

18. A surgical suture cutting device according to claim 15 wherein said trigger is attached to said handle via a pivot which allows for a movement of the trigger to press against said arcuate portion.

19. A surgical suture cutting device according to claim 15 wherein said distal suture guide further comprises (i) an open lateral suture guide slot being defined in part by a distal lateral wall and a dorsally facing lower wall and (ii) at least one curved guide area extending along a side surface of said distal suture guide, said curved guide area adjacent an end of said suture guide slot and extending distally and proximally from said suture guide slot along said distal suture guide.

20. A surgical suture cutting device according to claim 19 wherein a depth of said at least one curved guide area becomes more shallow from a deepest portion at a distal extent of said distal suture guide.

21. A surgical suture cutting device comprising:
a hollow shaft extending along a longitudinal axis between a proximal handle and a distal suture guide; and
a blade comprising an extension blade portion extending along said longitudinal axis between a proximal blade portion and a distal blade portion, said distal blade portion comprising a sharpened inclined cutting edge and being longitudinally movable between a first position and a second position, said proximal blade portion comprising (i) an arcuate portion ventrally extending from said extension blade portion and (ii) a spring extension ventrally extending from said arcuate portion, said spring extension providing a biasing force to at least partially effectuate a proximal longitudinal movement of said distal end portions of said blade from said second position to said first position, said arcuate portion of said blade configured to contact a trigger to effectuate a distal longitudinal movement of said distal blade portion from said first position to said second position, wherein said distal suture guide comprises (i) an enclosed blade guide slot being aligned with said longitudinal axis and being defined in part by a ventrally facing upper wall, (ii) an open lateral suture guide slot being positioned distal to said blade guide slot and being defined in part by a dorsally facing lower wall, and (iii) a relief slot being aligned with said longitudinal axis and being positioned distal said suture guide slot, wherein the sharpened inclined cutting edge is inclined to face away from said upper wall of said blade guide slot, to face away from a dorsal edge of said distal blade portion, and to face toward said lower wall of said suture guide slot;

wherein said dorsal edge of said blade comprises a distal tall portion near said cutting edge, (ii) a inclined portion proximally adjacent said tall portion, and (iii) a ventrally recessed short portion proximally adjacent said inclined portion, wherein dorsal movement of said distal blade portion is limited by an interaction between at least said inclined portion of said dorsal edge of said blade and of said upper wall of said blade guide slot during longitudinal movement of said blade between said first position and said second position, wherein said inclined portion of said dorsal edge is configured to be in contact with said upper wall of said blade guide slot for a predetermined longitudinal movement distance of said cutting edge such that dorsal movement of said cutting edge occurs simultaneously with said predetermined longitudinal movement distance, and wherein said proximal blade portion and said extension portion consist of a single length of blade material.

22. A surgical suture cutting device according to claim 21 wherein said distal suture guide further comprises at least one curved guide area extending along a side surface of said distal suture guide, said curved guide area adjacent an end of said suture guide slot and extending distally and proximally from said suture guide slot along said distal suture guide.

23. A surgical suture cutting device according to claim 22 wherein a depth of said at least one curved guide area becomes more shallow extending proximally from a deepest portion at a distal extent of said distal suture guide.

24. A surgical suture cutting device according to claim 21 wherein said suture guide slot is defined in part by dorsal facing, distal and proximal chamfered surfaces arranged to ease an insertion of a suture into said suture guide slot.

25. A surgical suture cutting device according to claim 21 wherein said relief slot is defined in part by a lower wall being inclined to proximately and dorsally face toward said cutting edge, and wherein in said second position, said cutting edge is urged against said lower wall of said relief slot.

26. A surgical suture cutting device according to claim 21 wherein said inclined portion of said dorsal edge is configured to be in contact with said upper wall of said blade guide slot for a predetermined longitudinal movement distance of said cutting edge such that dorsal movement of said cutting edge occurs simultaneously with said predetermined longitudinal movement distance.

27. The surgical cutting device according to claim 26 wherein said predetermined longitudinal movement distance is at least an expected thickness of a suture to be cut such that said dorsal movement of said cutting edge occurs throughout a cutting said suture.

* * * * *